United States Patent [19]
Henry

[11] Patent Number: 5,725,770
[45] Date of Patent: Mar. 10, 1998

[54] WASTE TREATMENT PLANT AND PROCESS

[75] Inventor: Dick P. Henry, Brisbane, Australia

[73] Assignee: Fungi-Gulp Pty. Ltd., Queensland, Australia

[21] Appl. No.: 704,595

[22] PCT Filed: Mar. 16, 1995

[86] PCT No.: PCT/AU95/00145

§ 371 Date: Sep. 16, 1996

§ 102(e) Date: Sep. 16, 1996

[87] PCT Pub. No.: WO95/25071

PCT Pub. Date: Sep. 21, 1995

[30]     Foreign Application Priority Data

Mar. 17, 1994  [AU]  Australia .................. PM 4520

[51] Int. Cl.$^6$ .................. C02F 3/12; C02F 11/14
[52] U.S. Cl. .......... 210/603; 210/612; 210/631; 210/764; 210/180; 210/201; 210/255
[58] Field of Search .................. 210/603, 605, 210/612, 613, 620, 621, 631, 764, 175, 177, 903, 179-183, 195.1, 199, 201, 255

[56]           References Cited

U.S. PATENT DOCUMENTS

| | | | |
|---|---|---|---|
| 4,246,099 | 1/1981 | Gould et al. | 210/603 |
| 5,228,995 | 7/1993 | Stover | 210/180 |
| 5,290,450 | 3/1994 | Kobayashi | 210/613 |
| 5,380,438 | 1/1995 | Nungesser | 210/605 |
| 5,470,481 | 11/1995 | Modell et al. | 210/175 |
| 5,514,277 | 5/1996 | Khudenko | 210/631 |
| 5,616,241 | 4/1997 | Khudenko | 210/195.1 |

FOREIGN PATENT DOCUMENTS

| | | |
|---|---|---|
| 13128/76 | 4/1976 | Australia . |
| 58023/80 | 11/1980 | Australia . |
| 85687/82 | 1/1983 | Australia . |
| 36004/84 | 6/1985 | Australia . |
| 56223/86 | 9/1986 | Australia . |
| 15279/88 | 11/1988 | Australia . |
| 16269/88 | 11/1988 | Australia . |
| 53620/90 | 8/1990 | Australia . |
| 52773/90 | 9/1990 | Australia . |
| 61544/94 | 9/1994 | Australia . |
| 087127 | 8/1983 | European Pat. Off. . |
| 60/084198 | 5/1985 | Japan . |
| 1151515 | 4/1985 | U.S.S.R. . |
| 1171436 | 8/1985 | U.S.S.R. . |
| 1404468 | 6/1988 | U.S.S.R. . |

OTHER PUBLICATIONS

Blachford, et al., "Oxygenated Activated-Sludge Process: Evaluation at Palmersford", Journal of the Institute of Water Pollution Control, vol. 81, No. 5, pp. 601-618, 1982.

*Primary Examiner*—Thomas G. Wyse
*Attorney, Agent, or Firm*—Madson & Metcalf

[57]           ABSTRACT

A waste treatment process including the steps of: (i) passing waste material which may comprise animal or human faeces comprising an insoluble component such as lignocellulose through a bioreactor system including a plurality of bioreactors in series and maintaining said insoluble component as a suspension in said waste material; and (ii) separating suitably by filtration the insoluble component from the waste material. A waste treatment plant including: (i) a bioreactor system including a plurality of bioreactors in series for treatment of waste material; (ii) means such as filtration for separating an insoluble component from said waste material after passage through the bioreactor system.

29 Claims, 2 Drawing Sheets

WASTE TREATMENT PLANT AND PROCESS

FIELD OF THE INVENTION

THIS INVENTION relates to a waste treatment plant and process.

BACKGROUND ART

Hitherto disposal of waste including faeces from livestock feedlots including piggeries, beef cattle feedlots, dairy cattle milking sheds and holding yards, and poultry farms which were operated on a large scale commercial basis has been a time consuming and expensive process. This was mainly because of the problem of effective disposal of an insoluble or undigested solid or sludge component which was mainly formed from animal faeces which was sometimes mixed with undigested livestock feed. Animal faeces contains proteins, protein breakdown products, fats, complex carbohydrates and lignocellulose. Lignocellulose is an amorphous matrix of hemicellulose and lignin. Hemicelluloses are polysaccharides which are usually branched and formed from sugars and uronic acids. Lignins are highly cross-linked aromatic polymers of no regular repeating unit because of their formation by free radical condensation. Lignocellulose in the animal faeces is derived from barley (e.g. barley awns), lucerne, sorghum and other stockfeeds.

Reference is made to Australian Patent Application 91080/91 (ie. International Patent Application PCT/AU91/00587 which was published under WO 92/11210) which describes a waste treatment process and plant which comprises passing biological waste through one or more hanging curtains made from two layers of a soft reticulated polyurethane foam and a reinforcing layer of synthetic material interposed therebetween. The curtains formed a support for filamentous micro-organisms which formed a dense mat of cellular material. The micro organisms remove dissolved phosphorus, nitrogen in the form of ammonia and carbon as organic acids from the biological waste.

The process of Specification WO 92/11210 was extremely efficient in processing biological waste from distilleries and breweries as well as glycerol waste because this waste did not require an initial anaerobic fermentation step which is necessary in relation to waste from livestock feedlots as described above. As stated in Specification WO 92/11210 non-fermented biological waste must be subjected to an anaerobic fermentation step so as to break down complex macromolecules such as carbohydrates, proteins, lipids to organic acids of 8 carbon atoms or less. This fermentation step takes place usually in the presence of acidogenic fermentative bacteria which may produce organic acids such as volatile fatty acids which may be readily metabolised to carbon dioxide by the hanging curtain technology described above.

After the fermentation period was completed which usually took 5 days or more soluble digestible matter was collected as supernatant and separated from the insoluble or undigested sludge component discussed above which contained lignocellulose.

The conventional methods for disposal of the indigestible material included passing the indigestible material to anaerobic ponds, septic tanks or pits. Alternatively the indigestible material was dewatered by filtration or by drying on open or covered sand beds. The dried sludge was subsequently incinerated or used as fertiliser. In some cases the indigestible material was used as landfill.

However it will be appreciated from the foregoing that the presence of the indigestible material in the anaerobic fermentation tank or digester meant that fermentation had to be stopped at periodic intervals of time to remove the indigestible material which was time consuming, wasteful and expensive.

The indigestible material also could not be spread onto anaerobic ponds or used as landfill in Moslem countries such as Malaysia or Indonesia. In countries where this method of disposal could be achieved, it was relatively expensive because of the transportation costs.

The presence of the indigestible material in the anaerobic digester also was undesirable in that it accumulated in the digester over a period of time and inhibited the fermentation reaction proceeding in an efficient manner because of the production of phenolic compounds. These compounds were also toxic to the filamentous micro-organisms used in the hanging curtain technology of Specification WO/9211210.

It will also be appreciated that the indigestible material also contained many pathogenic microorganisms after the anaerobic fermentation step which were not eradicated prior to the pumping of the indigestible material as a slurry into anaerobic ponds or when spread onto land and thus caused disease or infection. To avoid this possibility it was necessary, as discussed in Henry et al Journal Appl Bact. 55 89–95 (1983), to reduce the pH of the indigestible material to pH 4.5 or lower (ie. below the pKa of the volatile fatty acids). In this regard it will be appreciated that free volatile fatty acids can eliminate bacterial pathogens.

SUMMARY OF THE INVENTION

It therefore is an object of the invention to provide a process and plant for waste treatment which may alleviate at least to a certain extent the problems described above in regard to efficient disposal of the insoluble or undigested sludge component containing lignocellulose.

The process of the invention includes the following steps:

(i) passing waste material comprising an insoluble component through a bioreactor system including a plurality of bioreactors in series and maintaining said insoluble component as a suspension in said waste material;

(ii) passing treated waste material from said bioreactor system to one or more acidification tanks to reduce the pH below 4.5 to produce free volatile fatty acids for elimination of bacterial pathogens in said treated waste material; and (iii) separating the insoluble component from the waste material before or after step (ii).

There is also provided a waste treatment plant including:

(i) a bioreactor system including a plurality of bioreactors in series for treatment of waste material;

(ii) one or more acidification tanks to reduce the pH below 4.5 to produce free volatile fatty acids for elimination of bacterial pathogens in said treated waste material; and (iii) means for separating an insoluble component from said waste material after passage through the bioreactor system.

The waste material which is subject to the process of the invention suitably includes human or animal faeces and preferably faeces from livestock feedlots as described above which may have a stockfeed component containing lignocellulose.

Each bioreactor may be interconnected by an overflow conduit so that waste material or influent is quickly and efficiently transferred from one bioreactor to an adjacent bioreactor without the need for pumping material so as to transfer material from one bioreactor to another.

Each bioreactor is suitably provided with agitation means which keeps the contents of each bioreactor in the form of a slurry or suspension so that the solid particles are maintained in the suspended state to achieve the object of the invention.

The contents of each bioreactor are also suitably subject to appropriate heating means and in one form this may be provided by steam being passed into and out of each bioreactor. However, other forms of heating means may be utilised such as electrical heating. Preferably the temperature in each bioreactor is maintained at a desired temperature by suitably thermostatically controlled means between 25°–50° C. and more suitably 30°–40° C. In a preferred form the temperature is slowly decreased as the waste material passes through each bioreactor from initially 40° C. to finally 30° C.

Preferably the pH of the waste material fed into the bioreactors is maintained between 5.0–7.0 and more suitably between 5.8–6.4. The retention time in each bioreactor may be 12–48 but more suitably 24 hours.

After the waste effluent leaves the bioreactor system it may be passed through a filter or sieve to filter out the insoluble material which is preferably incinerated or if it is to be spread onto land it may be passed through acidification tanks as described hereinafter. It will be appreciated that removal of the insoluble material may take place in any suitable manner. While filtration is a preferred procedure, flocculation may also be utilised.

The supernatant or soluble liquid from the filter may then be passed into the one or more acidification tanks and preferably maintained in said tank(s) for a period of 24–48 hours to reduce the pH to a value of below 4.5 and more suitably between 4.0–4.5 which is below the pKa of the volatile fatty acids e.g. acetic acid, propionic acid, butyric acid, valetic acid, caproic acid, enanthic acid as well as octanoic acid as well as relevant isomers. Such volatile fatty acids (VFAs) are produced by the anaerobic bioreactor system and the lowering of the pH is to convert VFA salts to free acid in the acidification tank(s). This will eliminate most, if not all bacterial pathogens.

In a variation of the above described procedure, in some cases the waste effluent after it leaves the bioreactor system may be passed through the acidification tank(s) before removal of the insoluble material. In this embodiment after removal of the insoluble material the waste effluent may then be passed to a curtain assembly as described hereinafter. This procedure is preferable when it is impossible to incinerate the insoluble material after filtration of the waste material after passage of the waste material through the bioreactor system.

There also may be provided means for maintaining an atmosphere of carbon dioxide or other gas in said acidification tank(s) to inhibit the growth of yeasts in said acidification tank(s). Such means may, for example, comprise conduit(s) for the carbon dioxide or other gas which extend into the or each acidification tank. Such conduits may be connected to a suitable source of carbon dioxide or said other gas.

Preferably in this embodiment there is provided means such as appropriate transfer conduits for transferring effluent gases (which may include carbon dioxide) generated in the bioreactor system to the acidification tank(s) to maintain a gaseous atmosphere above the waste material being acidified. This feature as stated above is useful in that it inhibits the growth of yeasts or fungi in the acidification tank(s) such as *Candida ingens*. The gases may subsequently be removed from the acidification tank(s) by appropriate conduit(s) to gas scrubbers for eventual discharge.

Preferably the waste material is subjected to a further treatment step to remove nitrogen in the form of ammonia, dissolved phosphorous and carbon in volatile fatty acids. More preferably a suitable means for removing nitrogen in the form of ammonia, dissolved phosphorous and carbon is a hanging curtain assembly. In this particular embodiment, the waste from the acidification tank(s) may be passed to a hanging curtain assembly, which maybe, for example, a hanging curtain assembly of the of the type described in Patent Specification 91080/91. Some of the carbon is evolved as carbon dioxide with the remainder being retained by the micro-organisms contained therein in the hanging curtain assembly.

BRIEF DESCRIPTION OF THE DRAWINGS

Reference may now be made to a preferred embodiment of the invention as shown in the attached drawings wherein.

DETAILED DESCRIPTION

Figure 1:
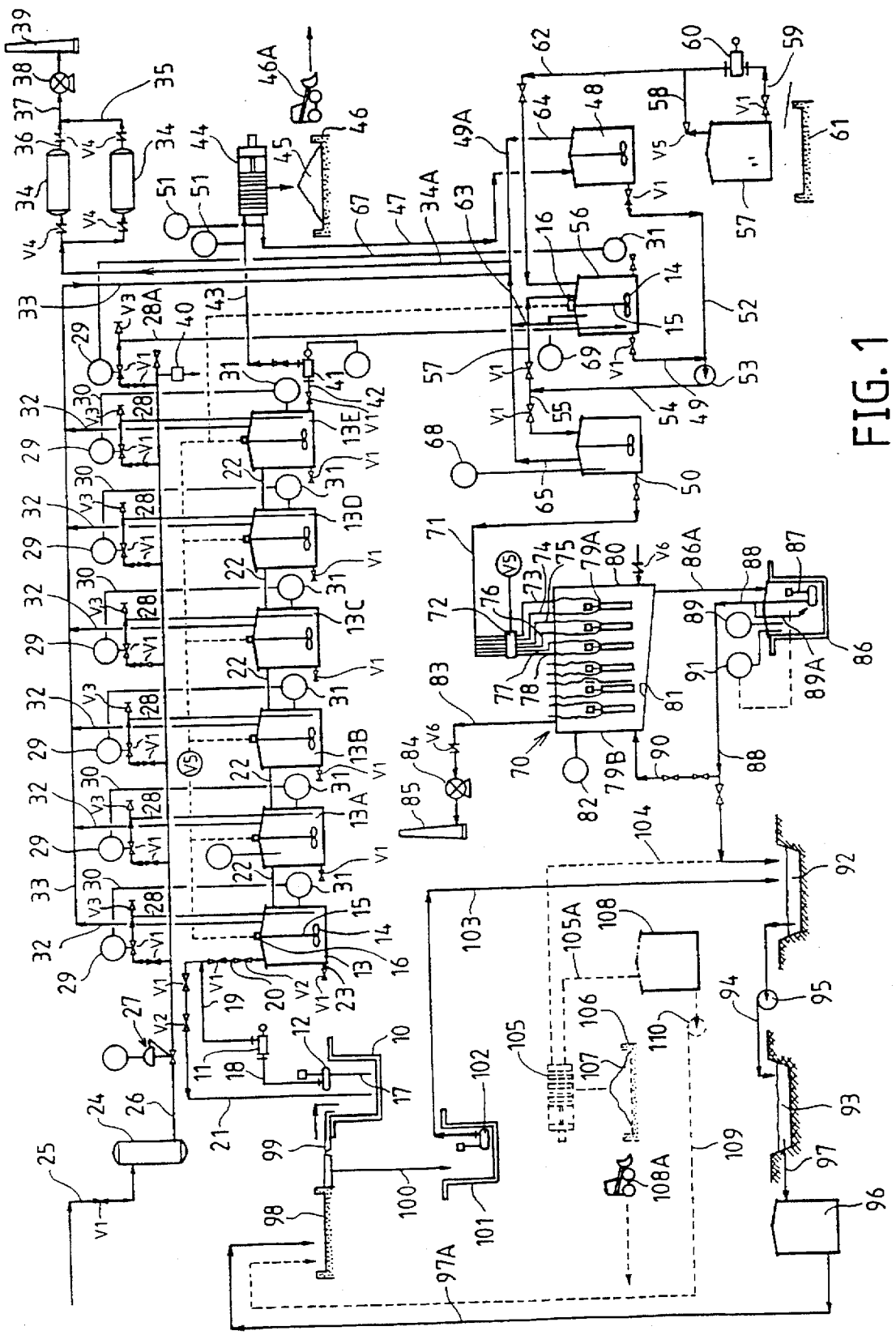
FIG. 1 is a flow diagram of a waste treatment plant constructed in accordance with the invention.

In FIG. 1 there is shown an in-ground holding tank 10 for influent comprising faeces admixed with undigested feed or waste feed from a piggery (not shown). The influent is pumped by a feed pump 11 through a macerator 12 which grinds the particles in the influent into small pieces or finely divided material before the influent is passed into bioreactor 13 provided with agitator 14 having shaft 15 mounted in bearing 16. There is also provided conduit between holding tank 10 and macerator 12, conduit 18 between feed pump 11 and macerator 12 and conduit 19 which provides communication between inlet conduit 20 and bioreactor 13. Conduit 20 is provided with a shut off valve $V_1$ and flow control diaphragm valve $V_2$. Conduit 21 functions as a return line for recycling influent from bioreactor 13 through conduit 20 back to holding tank 10 which depends upon operation of valves $V_1$ and $V_2$.

There is also provided additional bioreactors 13A, 23B, 13C, 13D and 13E all having a similar construction to bioreactor 13. There is provided overflow conduits 22 between adjacent bioreactors for transfer of fluid. Each bioreactor is also provided with a drain line 23 having a shut off valve $V_1$.

There is also provided a steam boiler 24 into which raw water is fed through conduit 25 also provided with a single valve $V_1$. Steam may then pass into conduit 26 having a pressure control valve assembly 27.

There is also provided a plurality of steam conduits 28 which each communicate with supply conduit 26 as shown which pass steam into each of the bioreactors 13–13E as shown. Each steam conduit 28 is also provided with a vacuum breaker valve $V_3$ to stop back siphonage of fluid as shown. There is also provided a shut off valve $V_1$ in each conduit 28 as well as a further valve $V_1$ associated with a temperature control valve 29 in the form of a sliding gate valve associated with conduit 30 which also has a thermostat or thermostat controller 31 in the form of a probe which extends into each bioreactor which controls the temperature attained in each bioreactor 13–13E.

There is also provided an outlet conduit 32 with each bioreactor 13–13E which each communicates with conduit 33 for passing effluent gases to tanks 48, 50 and 56 described hereinafter via transfer conduit 32A and inlet conduits 33A, 33B, and 33C. Effluent gases may then pass through a return line 34A from gas line 49A to a pair of gas scrubbers 34 connected in parallel as shown. The bottom gas scrubber 34 has an associated conduit 35 and the top gas scrubber 34 has an associated conduit 36. Each of conduits 35 and 36 are shut off with valves $V_4$ and communicate with conduit 37 which communicates with fan 38 and stack 39. There is also provided steam trap 40. Valves $V_4$ function to take one of scrubbers 34 out of service for maintenance purposes.

The effluent after it passes out through the final bioreactor 13E is passed through a feed pump 41 through conduit 42 and subsequently through conduit 43 to a sludge filter 44. Pressure indicators 51 are shown associated with conduit 43 as well as conduit 47. A solid fraction 45 from sludge filter 44 is retained in container 46 whereby solid fraction 45 which is mainly lignocellulose may be transferred by truck 46A for incineration or other form of disposal. A liquid fraction rich in volatile fatty acids or VFAs is then passed to a VFA feed tank 48 through conduit 47 where it is held for 2 days before being passed through conduit 52 to a transfer pump 53 before being fed into VFA holding tank 50 via conduit 54 which communicates with conduit 55.

Conduit 28A functions to transfer steam from conduit 26 to a VFA liquid acidification tank 56 which is fed with sulfuric acid ($H_2SO_4$) from a sulfuric acid feed tank 57 which is associated with an inlet conduit 58 having a pressure relief valve $V_5$ and a drain conduit 59 which communicates with conduit 62 which passes through a sulfuric acid pump 60. There is also provided a sump 61. The sulfuric acid is passed through conduit 62 which communicates with conduits 58 and 59 as shown to acidification tank 56 which is also provided with an agitator 14 as shown. Each of agitators 14 and associated shafts 15 in bioreactors 13—13E as well as tank 56 are provided with a variable speed control (VS) shown in phantom. Material may be passed from tank 56 to conduit 52 through conduit 49 which thereafter may be transferred to conduit 55 and hence to tank 50 or alternatively to tank 56 though conduit 57 depending upon operation of shut off valves $V_1$.

There is also provided conduits 64, 63 and 65 which each communicate with tanks 48, 56 and 50 respectively for transferring effluent gases back into gas line 49A and subsequent flow through return line 34A. Conduit 67 is also shown having temperature controller 31 for control of temperature in tank 56. Conduit 67 communicates with conduit 28A as shown via temperature control valve 29.

Tank 50 is also provided with temperature indicator 68 and tank 56 is also provided with pH indicator 69 as shown.

Liquid from VFA holding tank 50 is passed to a hanging curtain assembly 70 through conduit 71 and passed through a curtain feed pump 72 provided with a variable speed control VS. Conduit 71 may be split into separate conduits 73 and 74, 75 and 76 as well as 77 and 78 which may apply liquid waste as shown to either side of a curtain module or curtain subassembly 79A. There also may be utilised three additional sub-assemblies 79B if required to increase the waste treatment capacity of hanging curtain assembly 70. The flow connections of sub-assemblies 79B to pump 72 are omitted for clarity. Each of sub-assemblies 79A and 79B are retained in a housing 80 having a sloping drain floor 81. There is also utilised a temperature indicator 82 which is associated with housing 80.

Gases from housing 80 may be passed through conduit 83 through damper valve $V_6$, cooling fan 84, and stack 85. There is also shown a further damper $V_6$ which communicates with the interior of housing 80 and the operation of each damper valve $V_0$ controls air flow through housing 80. Preferably the air pressure inside housing 80 is maintained less than atmospheric.

Waste effluent may be passed from the sloping floor 81 of housing 80 to a treated waste holding tank 86 having a discharge pump 87 associated therewith via conduit 86A. There is also provided a level element 91 which may control pump 87 for maintaining the level of fluid in housing 80. There is also provided pH indicator 89. Fluid may be pumped by pump 87 through discharge conduit 88 which has a return line 89A. Waste may be recycled through conduit 90 to housing 80 as shown from conduit 88. Thereafter waste may be passed to a treatment pond 92 which communicates with another pond 93 via conduit 94 with the assistance of pump 95. Waste may subsequently be transferred to a feed tank 96 via conduit 97. Thereafter conduit 97A may pass fluid to a treatment channel or flume 98 of a piggery. Subsequently fluid may be passed to holding tank 10 via a bypass plate 99 or alternatively through a conduit 100 to an in ground holding tank 101 having a discharge pump 102 which may transfer fluid to treatment pond 92 through conduit 103.

In an alternative arrangement as shown in phantom material from conduit 88 may be transferred through conduit 104 to a filter 105 whereby a solid fraction 107 may be deposited in container 106 before being removed by truck 108A for incineration or other form of disposal. A liquid fraction may be passed from filter 105 via conduit 105A to a liquid tank whereby it may be recycled to flume 98 via conduit 109 and with the assistance of pump 110.

Figure 2:
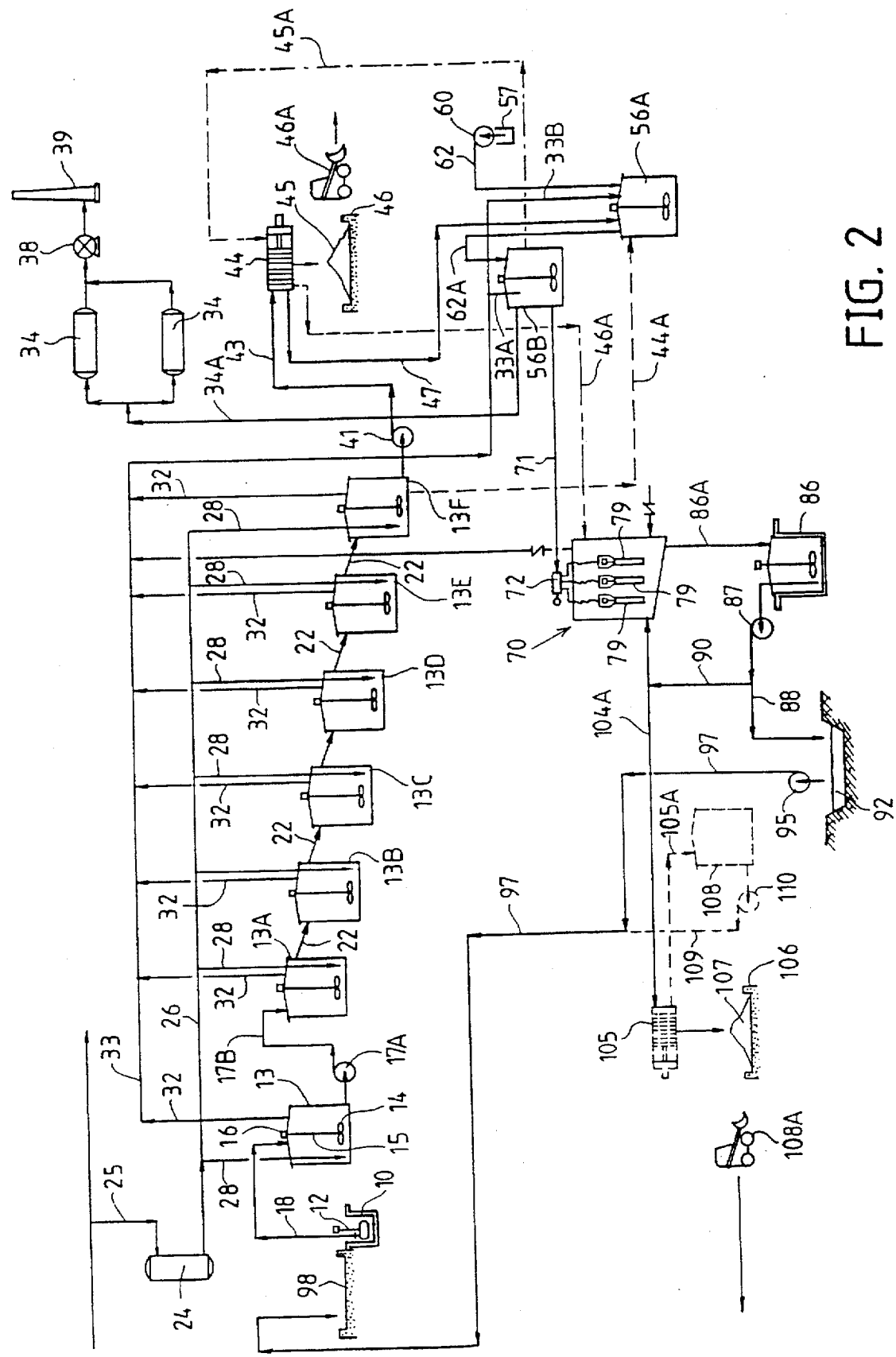
FIG. 2 is a flow diagram of an alternative form of waste treatment plant constructed in accordance with the invention.

FIG. 2 represents a modified waste treatment plant in contrast to the waste treatment plant shown in FIG. 1. Similar reference numerals are utilised for the sake of convenience. One difference between the FIG plant and the FIG. 2 plant is the adoption of bioreactors 13–13F on a slope as indicated with overflow conduits 22 facilitating transfer of fluid from adjacent bioreactors. Valves are also not indicated for the sake of convenience. One conduit 18 interconnects holding tank 10 and bioreactor 13 and steam from boiler 24 flows through conduit 26 and subsequently through inlet conduits 28 to a respective bioreactor 13–13F. Exhaust conduits 32 for gas also communicate with main transfer conduit 33 as described above in the FIG. 1 waste treatment plant.

Gas is passed to acidification tanks 56A and 56B through conduit 33 and into each tank through inlet conduits 33A and 33B as shown. There is also supplied a gas return line 34A to gas scrubbers 34.

In a variation of the procedure shown in FIG. 1, the waste effluent or waste material after emerging from the final bioreactor 13F may be transferred directly to acidification tank 56A through conduit 44A shown in phantom. In this variation the waste material will still have the insoluble component entrained therein so that the waste material may then be transferred from acidification tank 56B to filter 44 after passage through conduit 45A also shown in phantom. Subsequently, after filtration the liquid fraction may then be transferred to curtain assembly 70 through conduit 46A also shown in phantom.

Another difference is the adoption of two VFA liquor acidification tanks 56A and 56B whereby a liquid fraction from sludge filter 44 is passed through conduit 47 and subsequently into tank 56A. Sulphuric acid is pumped by pump 60 from a tank or drum 57 via conduit 62 to tank 56A. Material may then be passed from tank 56A to tank 56B through conduit 62A. Acid treated fluid may then be passed to curtain assembly 70 through conduit 71.

Waste liquid after passing through curtain assembly 70 is passed to filter feed tank 86 through conduit 86A whereafter fluid is pumped by pump 87 to treatment pond 92 by conduit 88 or passed through recycling conduit 90 to curtain assembly 70 after passage through conduit 104A. Liquid from pond 92 is passed through conduit 97 back to flume 98 with the agency of pump 95. Fluid may also be passed to filter 105 from curtain assembly 70 through conduit 104A whereby a liquid fraction may be passed to treatment tank 108 through conduit 105A whereafter fluid may be passed to conduit 97 through conduit 109 assisted by pump 110.

The waste being passed through the series of bioreactors is serially digested by a different population of flora in each tank. The short mean residue time in each tank (~24 hours) permits a specific flora to develop in each tank and progressively digest the material being passaged. The end result is the product of volatile fatty acids (VFAs) i.e. $C_2$–$C_8$ (acetic, propionic, butyric, valeric, caproic, heptanoic and octanoic acids and relevant isomers). Non-volatiles such as lactic and/or succinic acids are not produced. Traces (~3 $mML^{-1}$) of phenylacetic acid do appear. The purpose of restricting the end products of fermentation to VFAs ensures an excess of these acids is present to effect destruction of bacterial pathogens present in the waste.

The serial fermentation also enables conditions of pH, fermentation and residue time in each bioreactor to be manipulated in order to optimise production of the VFAs.

| WASTE TREATMENT PLANT DESIGN CRITERIA | |
|---|---|
| 1.0 GENERAL | |
| Atmospheric Pressure | 101.325 kPa |
| Min Design Temperature | 15° C., 50% relative humidity |
| Max Design Temperature | 32° C., 100% relative humidity |
| Operating Schedule | 7 days/week, 24 hours/day |
| 2. FEED DEFINITION | |
| Feed Material | Piggery flume floor flushings |
| Treatment Capacity | 1500 L/day |
| Feed % Solids | 3% w/v |
| Solids Size Range | 2–5 mm |
| Feed pH | 5.8–6.4 |
| Design Temperature - Min | 20° C. |
| Design Temperature - Max | 30° C. |
| Design Availability | 85% |
| Design Flow | 73.5 L/h |
| 3.0 FEED TANK | |
| Type | Inground |
| Material | Concrete |
| Retention Time | 24 hours |
| Capacity | 1500 L nominal |
| Temperature | 20° C.–30° C. |
| 4.0 ANAEROBIC BIOREACTORS | |
| No. Stages | 6 |
| Retention Time per stage | 24 hours |
| Temperature Reaction | 1 40° C. |
| | 2 35° C. |
| | 3 35° C. |
| | 4 35° C. |
| | 5 30° C. |
| | 6 30° C. |
| % of solids fermented | 45% |
| Tank material | FRP (Isophthalic) |
| Agitation | Suspension (0.25 kW/m³ approx) S.S. 316 A310 impeller |
| 5.0 FERMENTATION PRODUCT | |
| pH | 5.8–6.4 |
| Temperature | 30° C. |
| % Solids | 1.5% w/v |
| Solids Composition | Lignocellulose |
| 6.0 POST FERMENTATION FILTRATION | |
| Filtration Rate | L/m² · h |
| Filter Cake Moisture | % moisture wet basis |
| Product Calorific Value | 20 MJ/kg, air-dry |
| Kg Product per Day | 25 |
| 7.0 ACIDIFICATION | |
| Retention Time (batch) | 48 hours |
| No. Tanks | 3 (series batch) |
| pH after Acidification | 4.5 |
| Acid Addition Rate | 2–3 mL $H_2SO_4$ per L filtrate |
| Temperature | Natural |
| Acid Consumption | 3–4.5 L/day |
| Acid Storage | 200 L drums |
| Acid Delivery | Via drum pump or manual container addition |
| 8.0 FEED TO CURTAINS Analysis | | |
| Acetic Acid | 137 mmol/L | 0.82% w/V |
| Propionic Acid | 37 mmol/L | 0.27% w/v |
| Butyric Acid | 38 mmol/L | 0.33% W/V |
| Valeric Acid | 10 mmol/L | 0.10% w/v |
| Caproic Acid | 3.1 mmol/L | 0.04% w/v |
| Total Volatile Fatty Acids | | 1.57% w/v |
| Feed rate - average | | 62.5 L/h |
| - design | | 73.5 L/h |
| pH | | 4.5 |
| Temperature | | 30° C. |
| 9.0 CURTAIN MODULE | | |
| Curtain Treatment Capacity | | 40–100 L/m² day |
| No. Curtains | | 3 |
| Curtain Fall | | 3 m or greater |
| Operating Temperature - Max | | 37° C. |
| Air Temp in | | 28° C.–32° |
| % Relative Humidity | | 90% |
| % Relative Humidity | | 100% |
| Distance between curtains | | 150 mm |

I claim:

1. A waste treatment process including the steps of:
   (i) passing waste material comprising an insoluble component through a bioreactor system including a plurality of bioreactors in series and maintaining said insoluble component as a suspension in said waste material;
   (ii) passing treated waste material from said bioreactor system to one or more acidification tanks to reduce the pH below 4.5 to produce free volatile fatty acids for elimination of bacterial pathogens in said treated waste material; and
   (iii) separating the insoluble component from the waste material before or after step (ii).

2. A process as claimed in claim 1 including a further step of treating waste material to remove nitrogen in the form of ammonia, dissolved phosphorous and carbon as volatile fatty acids.

3. A waste treatment process as claimed in claim 1 wherein said waste material is agitated each bioreactor so that said waste material is maintained in the form of a slurry or suspension to maintain said insoluble component in a suspended state.

4. A waste treatment process as claimed in claim 1 wherein said waste material in each bioreactor is heated to a temperature of between 25°14 50° C.

5. A waste treatment process as claimed in claim 4 wherein the temperature is maintained between 30°–40° C.

6. A waste treatment process as claimed in claim 5 wherein the waste material is initially at a temperature of 40° C. in said bioreactor system before the temperature is slowly decreased to 30° C.

7. A waste treatment process as claimed in claim 1 wherein the pH in said bioreactor system is maintained between 5.0–7.0.

8. A waste treatment process as claimed in claim 7 wherein the pH is maintained between 5.8–6.4.

9. A waste treatment process as claimed in claim 1 wherein said waste material is maintained in each bioreactor for 12–48 hours.

10. A waste treatment process as claimed in claim 9 wherein said waste material is maintained in each bioreactor for 24 hours.

11. A waste treatment process as claimed in claim 1 wherein the waste material after leaving the bioreactor system is passed through a filter or sieve to filter out the insoluble component.

12. A waste treatment process as claimed in claim 11 wherein a liquid fraction remaining after removal of the insoluble component is passed into said one or more acidification tanks for a period of 24–48 hours.

13. A waste treatment process as claimed in claim 2 wherein said waste material after passage through said one or more acidification tanks is passed through a hanging curtain assembly for removal of said nitrogen in the form of ammonia, dissolved phosphorous and carbon as volatile fatty acids.

14. A waste treatment process as claimed in claim 1 wherein the pH is reduced to a value of between 4.0–4.5.

15. A waste treatment process as claimed in claim 1 wherein an atmosphere of carbon dioxide or effluent gases is maintained in the or each acidification tank to inhibit growth of bacterial pathogens.

16. A waste treatment plant including:
(i) a bioreactor system including a plurality of bioreactors in series for treatment of waste material;
(ii) one or more acidification tanks to reduce the pH below 4.5 to produce free volatile fatty acids for elimination of bacterial pathogens in said treated waste material; and
(iii) means for separating an insoluble component from said waste material after passage through the bioreactor system.

17. A waste treatment plant as claimed in claim 16 wherein each bioreactor is connected to an adjacent bioreactor by transfer conduit.

18. A waste treatment plant as claimed in claim 16 wherein each of said bioreactors are supported on a slope with an initial bioreactor located on a more elevated position than a final bioreactor.

19. A waste treatment plant as claimed in claim 16 wherein there is provided heating means in each bioreactor to maintain an operational temperature of between 30°–40°.

20. A waste treatment plant as claimed in claim 19 wherein said heating means includes means for injection of steam into each bioreactor.

21. A waste treatment plant as claimed in claim 20 wherein there is provided a steam boiler connected to a steam conduit which is connected to injection conduits which communicate with each bioreactor.

22. A waste treatment plant as claimed in claim 19 wherein there is provided thermostatically controlled means to maintain said operational temperature in each bioreactor.

23. A waste treatment plant as claimed in claim 16 wherein each bioreactor is provided with agitation means to maintain said waste treatment material in a suspended state.

24. A waste treatment plant as claimed in claim 16 wherein said separating means includes a filter or sieve to separate said insoluble component from a liquid fraction of said waste material.

25. A waste treatment plant as claimed in claim 16 wherein there is provided means to maintain an atmosphere of carbon dioxide or other gas in said acidification tank(s) to inhibit growth of yeasts.

26. A waste treatment plant as claimed in claim 25 wherein said means to maintain an atmosphere of carbon dioxide includes transfer means to transfer effluent gases generated in said bioreactor system to said acidification tank(s).

27. A waste treatment plant as claimed in claim 26 wherein said gases from said acidification tank(s) are transferred to gas scrubbers for discharge.

28. A waste treatment plant as claimed in claim 16 wherein there is further provided a treatment means in communication with said one or more acidification tanks to remove nitrogen in the form of ammonia, dissolved phosphorous and carbon as volatile fatty acids from said waste material.

29. A waste treatment plant as claimed in claim 28 wherein said treatment means includes a hanging curtain assembly.

* * * * *